United States Patent [19]

Murakami et al.

[11] 4,157,332

[45] Jun. 5, 1979

[54] HEAT-SENSITIVE THIAZOLIUM-7,7,8,8-TETRACYANOQUINODIMETHANE SEMICONDUCTIVE MATERIALS

[75] Inventors: Mutsuaki Murakami; Susumu Yoshimura, both of Kawasaki, Japan

[73] Assignee: Matsushita Electric Industrial Co., Ltd., Japan

[21] Appl. No.: 805,342

[22] Filed: Jun. 10, 1977

[30] Foreign Application Priority Data

Jun. 11, 1976 [JP] Japan .................................. 51/69052
Jun. 11, 1976 [JP] Japan .................................. 51/69053
Jun. 11, 1976 [JP] Japan .................................. 51/69055

[51] Int. Cl.² ............................................. C07D 277/22
[52] U.S. Cl. ................................. 260/302 R; 546/348
[58] Field of Search .................................. 260/302 R

[56] References Cited

U.S. PATENT DOCUMENTS

3,941,792  3/1976  Murakami ........................ 260/286 Q

Primary Examiner—Jose Tovar
Attorney, Agent, or Firm—Lowe, King, Price & Becker

[57] ABSTRACT

Novel organic heat-sensitive semiconductive materials containing tetracyanoquinodimethane (TCNQ) as electron acceptor and exhibiting inherent resistivity-temperature characteristics. The materials include (N-n-propylthiazolium)$^+$(TCNQ)$^-$(TCNQ), (N-n-butylthiazolium)$^+$(TCNQ)$^-$(TCNQ) and (N-n-butylpyridium)$^+$(TCNQ)$^-$(TCNQ). These three compounds can be prepared by reacting TCNQ with iodides of corresponding cations, respectively. The heat-sensitive materials have particular utility in the field of timing or heat-sensitive elements.

3 Claims, 13 Drawing Figures

HEAT-SENSITIVE THIAZOLIUM-7,7,8,8-TETRACYANOQUINODIMETHANE SEMICONDUCTIVE MATERIALS

This invention relates to novel organic semiconductive materials and more particularly, to hitherto undescribed heat-sensitive ion radical or charge transfer complex materials of the type which contains 7,7,8,8-tetracyanoquinodimethane (hereinlater referred to simply as TCNQ) as electron acceptor. The present invention is also concerned with a timing element using the heat-sensitive materials of the type just mentioned.

Several compounds have been known to have resistance characteristics rapidly variable with temperature, including inorganic compounds such as oxides of titanium, vanadium, etc., and organic compounds such as TCNQ compounds. Typical of the inorganic compounds which have varying resistance in relation to temperature is $VO_2$ whose resistance rapidly varies in the order of magnitude of about $10^5$ in the vicinity of 70° C. $VO_2$ has been in use as detecting elements in a variety of temperature controlling devices. However, $VO_2$ has a disadvantage that its rapidly variable temperature range is as narrow as 46° to 80° C. By some reason inherent to $VO_2$ or other, the operative temperature range of the currently employed $VO_2$ elements is limited to only 60° C. to 70° C.

TCNQ compounds generally have a molecular structure expressed by a formula, $M^+(TCNQ)^-(TCNQ)_m$, in which $M^+$ represents a metal or organic cation. TCNQ compounds with $m=0$ are called simple salts, whereas those with $m \neq 0$ are called complex salts. With a very few exceptions, the crystals of these TCNQ compounds are characterized in that TCNQ molecules are stacked to form a column. The binding force between the TCNQ molecules in the vertical direction is very weak, so that the TCNQ molecules are mainly bonded one-dimensionally to provide an ideal state of crystals. Such one-dimensionally bonded crystals are in most cases physically unstable and are susceptible to changes in crystalline arrangement, depending on temperature or pressure, resulting frequently in a so-called phase transition.

The crystallization of TCNQ compounds are, more or less, influenced by such unstability to give rise to crystals which have a polymorphic crystalline structure or a non-stoichiometric composition.

Many studies have been directed to the phase transition of TCNQ complex salts to uncover their reversible and irreversible phase transition phenomena. These phase transition phenomena are observed as an anomaly in resistance-temperature characteristics at a phase transition point ($T_c$). Typical of the TCNQ compounds which show such anomaly in resistance-temperature characteristics are alkali metal-TCNQ simple salts such as Rb(TCNQ), Na(TCNQ), K(TCNQ), etc. These simple salts are particularly indicated by J. G. Vegter (Chem. Phs. Lett., Vol. 3, page 427 (1969)). While, some TCNQ complex salts are also known to show the resistance anomalies, typical of which is $[(C_6H_5PCH_3)]_{1-x}+[(C_6H_5)_3AsCH_3]_{3x}+(TCNQ)_2$ ($0 < X < 1$). This is discussed in detail by Kepler, et al., (J. Chem, Phys., Vol. 39, page 1311 (1963)). Another example of the TCNQ complex salt which shows the resistance anomaly is N-n-propylpyridium(TCNQ)$_2$, which we proposed in our prior application (Japanese Laid-open Application No. 45685/1976). All of the above-mentioned TCNQ compounds have a rapidly varying resistance at a temperature range above a normal temperature. Tetrathiofulvalenium (TCNQ) is known to have a rapidly varying resistance at a much lower temperature ($T_c = -215°$ C.). However, any of these TCNQ salts is too small in resistance variation, i.e., at most 3 to 5 times the initial value, and thus practically unsatisfactory to serve heat-sensitive material. There is accordingly a strong demand of a heat-sensitive material which exhibit a much greater resistance variation.

On the other hand, when these known TCNQ compounds undergo a phase transition, it is general that they have a lower resistivity on a higher temperature side and a higher resistivity on a lower temperature side. This is true of known inorganic heat-sensitive compounds including oxide, titanium oxide, etc. However, in case where the heat-sensitive materials having such specific resistivity-temperature characteristics are used as an element for control devices or overheat-preventing devices, it may be rather advantageous or practically useful if they have an increased resistivity on higher temperature side, even only two or three times larger resistivity. In this regard, an inorganic barium titanate-base compound is known to have an increased resistivity on higher temperature side and used to produce the positive temperature coefficient (PTC) thermisters. However, it has not been realized up to now to produce organic semiconductive materials, particularly TCNQ compounds, having the PTC characteristics.

It is therefore an object of the present invention to provide novel heat-sensitive semiconductive materials which contain as electron acceptor tetracyanoquinodimethane.

It is another object of the present invention to provide novel heat-sensitive semiconductive materials which have greatly and abruptly varied resistivity in certain temperature ranges.

It is a further object of the present invention to provide novel heat-sensitive semiconductive materials which have PTC characteristics.

It is a still further object of the present invention to provide a heat-sensitive semiconductive composition using the novel heat-sensitive semiconductive materials of the type mentioned above.

It is another object of the present invention to provide a heat-sensitive element using the novel heat-sensitive semiconductive materials of the type mentioned above.

The heat-sensitive semiconductive materials according to the invention is a member selected from the group consisting of (N-n-propylthiazolium)$^+$(TCNQ)$^-$(TCNQ) expressed by the following formula

-continued (N-n-butylthiazolium)+(TCNQ)−(TCNQ) expressed by the following formula (N-n-butylpyridium)+(TCNQ)−(TCNQ)

The heat-sensitive semiconductive materials of the invention can be broadly classified into two categories: the first category including (N-n-propylthiazolium)+(TCNQ)−(TCNQ) complex (hereinlater referred to simply as (NPPy) (TCNQ)$_2$) which has an abrupt decrease in resistivity in a certain temperature range; and the second category including the (N-n-butylthiazolium)+(TCNQ)−(TCNQ) complex (hereinlater referred to simply as (NBTh) (TCNQ) and the (N-n-butylpyridium)+(TCNQ)−(TCNQ) complex (hereinlater referred to simply as (NBPy) (TCNQ) which have the PTC characteristics, i.e., increasing resistivity in certain temperature ranges.

The other objects and advantages of the invention will become apparent as the specification proceeds.

Attention now is particularly directed to the accompanying drawings, in which.

The three TCNQ complex salts are prepared in a similar manner by known techniques. In broad aspect, it will suffice to mix TCNQ with an iodide of a corresponding organic cation, i.e., N-n-propylthiazolium, N-n-butylthiazolium or N-n-butylpyridium iodide, in a solvent under mild refluxing conditions. The reaction solution is allowed to stand overnight for crystallization at a suitable temperature of about 5° to 15° C. and the resulting crystals are separated and washed with the solvent and then ethyl ether. Suitable solvents are, for example, acetonitrile, acetone and methylene chloride. The washed crystals are recrystallized in sufficiently purified solvent such as acetonitrile two or three times to obtain a crystalline product. Upon the recrystallization, crystals stepwise appear first in 1 to 2 hours and then in a sufficient length of time, say, 1 to 4 days. That is, two or more kinds of crystals having different appearances are obtained in the form of a needle, a rod or a cross therebetween.

The form of crystals is greatly dependent on recrystallization conditions including concentration of solution, temperature and cooling rate of solution. For example, the needle crystals obtained initially are generally produced at a higher concentration and at a temperature of about 30° C., while the rod crystals are obtained from the solution from which the needle crystals are removed, after being allowed to stand over 1 to 4 days at about 5° C.

The elementary analysis reveals that the TCNQ complex salts in different crystalline forms have a TCNQ to cation molar ratio of about 2:1.

When the starting iodides are varied in amout in relation to TCNQ in the range of molar ratio of 2:1 to 1:1, the resulting TCNQ complex salts are found to have a TCNQ to cation ratio of about 2:1 when determined by the elementary analysis.

The synthetic methods and resistivity-temperature characteristics of the three heat-sensitive materials according to the invention are given in more detail below.

(NPTh) (TCNQ)$_2$

Synthesis

The preparation of the complex salt having a cation to TCNQ ratio of 1:2 is carried out, for example, by adding to a solution of 10 millimoles of TCNQ in 200 ml of acetonitrile 7.5 millimoles of N-n-propylthiazolium iodide dissolved in 20 ml of acetonitrile and refluxing the mixture at about 83° C. for 5 minutes. The reaction solution is allowed to stand at 5° C. overnight and the resulting crystals are separated and washed with acetonitrile and then ethyl ether. The thus washed crystals are dissolved in acetonitrile under refluxing conditions and allowed to stand at room temperature for recrystallization. As a result, black needle crystals with a specific resistance of 2900 Ωcm are first obtained at about 30° C. in 1 to 2 hours and rod crystals are then obtained when the solution from which the needle crystals have been separated is allowed to stand at 5° C. The optical analysis of the crystals in the wavelength range of ultra-violet or visible light reveals that the neutral TCNQ content in 1 mole of the salt is about 1 mole, thus the salt being a complex salt having a cation to TCNQ ratio of 1:2. According to the elementary analysis, the crystalline product is found to contain: C=67.3%; H=3.36% and N=23.51%. This result almost coincides with the analyses calculated: C=67.16%; H=3.36%; N=23.51% and S=5.97%. The crystalline salt has not a definite melting point but is decomposed in the vicinity of 200° C. When ratios of TCNQ to starting N-n-propylthiazolium iodide are varied in the range of 1:2 to 1:1, similar results are obtained.

Resistivity-Temperature Characteristics

Figure 1:
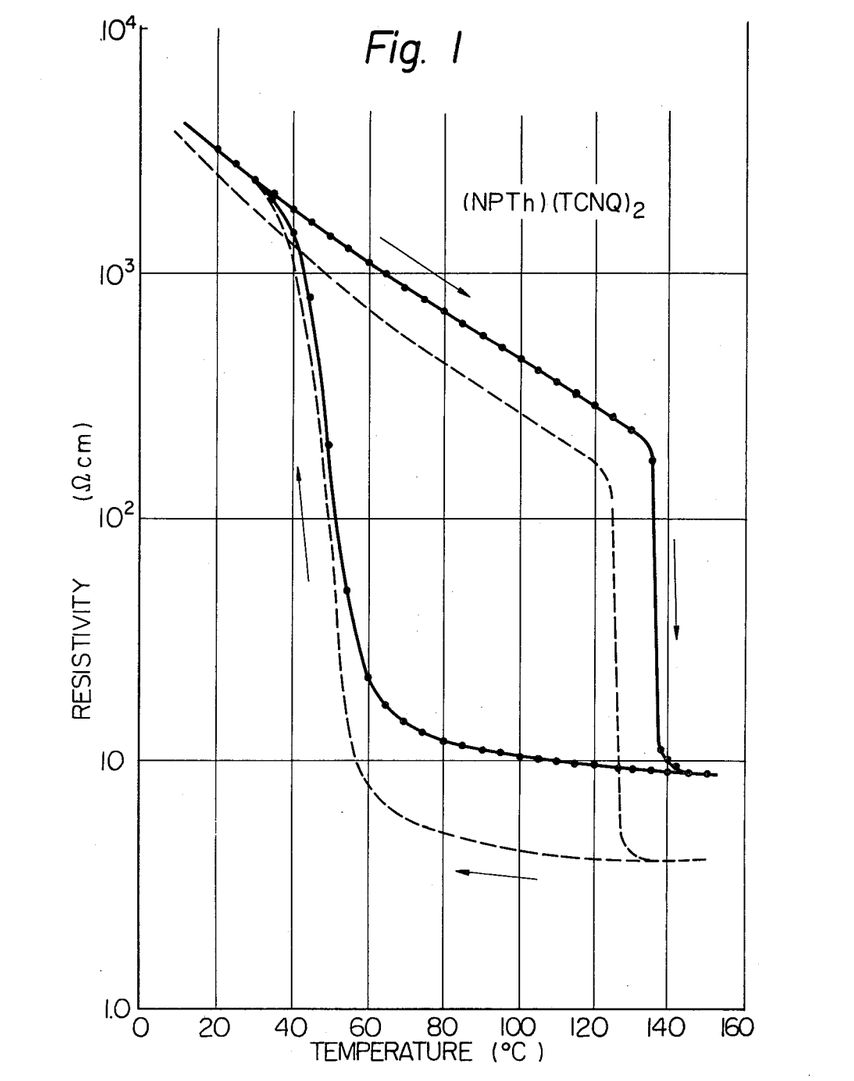
FIG. 1 is a graphical representation of specific resistance of a heat-sensitive semiconductive material according to the invention in relation to temperature.

With reference to FIG. 1, there are shown typical resistivity-temperature characteristics of a press molding of (NPTh) (TCNQ)$_2$ powder, which are obtained by a four-probe method using silver paste. In this figure, the curve indicated by dotted line shows the irreversible resistivity-temperature characteristics in the first cycle of temperatures, i.e., the first heating and cooling cycle, while that indicated by solid line is the reversible resistivity-temperature characteristics in the second and subsequent temperature cycles. In the second and subsequent temperature cycles, the resistivity is abruptly reduced down to 1/25 when heated to about 130°–138° C., returning to the original level when cooled to in the vicinity of 40°–60° C. That is, this phenomenon involves a temperature hysteresis, which is one of the prominent features of the invention. It has been proved through several hundreds cycles that the same reversible resistivity characteristics repeat after the second cycle. The resistivity-temperature characteristic cycle in the direction of arrows always takes place whenever the heating and cooling are repeated. Similarly, the arrows in other figures indicate the cycle of resistivity variation which occurs when the sample is heated and then cooled.

The reversible resistivity characteristics of the (NPTh) (TCNQ)$_2$ complex only slightly vary with the kind of the complex salt crystals. However, the different types of the (NPTh) (TCNQ)$_2$ crystals have almost the same variation point of resistivity and stability of the resistivity characteristics, and thus have substantially the same resistivity-temperature characteristics. It should be noted that the (NPTh) (TCNQ)$_2$ complex salt must be once heated to temperatures above the phase transition point on the higher temperature side, i.e., 140° C., so as to induce the reversible resistivity cycle in the second and subsequent temperature cycle. This is true of (NPPy) (TCNQ)$_2$ and (NPTh) (TCNQ)$_2$.

The observation of crystalline structure by an X-ray diffraction and the measurement by a differential scanning calorimeter (DSC) reveal that the anomal resistivity-temperature characteristics of the TCNQ complexes is due to a first order phase transition resulting from a change in crystalline structure.

The (NBPy) (TCNQ)$_2$ complex salt will be then described which has a heat-sensitive property of a specific type (i.e., PTC characteristics) that its resistivity increase to 2 to 3 times greater at about 138° C. and returns to the original low level at about 110° C. in a reversible manner.

Synthesis

The (NBPy) (TCNQ)$_2$ can be prepared in a manner similar to the case of the (NPTh) (TCNQ)$_2$. To a solution of 15 moles of TCNQ in 300 l of acetonitrile is added 7.5 moles of N-n-butylpyridinium iodide prepared by a known method, followed by reaction under refluxing conditions for 15 minutes. The reaction solution is allowed to stand in a thermostatic chamber of 5° C. overnight. The resulting black (NBPy) (TCNQ)$_2$ crystals are separated by a glass filter and washed with first acetonitrile and then ether to remove free iodine, and finally dried. By the reaction, the (NBPy) (TCNQ)$_2$ salt is obtained at a yield of 75 to 80%. The crystals are purified by recrystallizing it in sufficiently purified acetonitrile 2 or 3 times. According to recrystallization conditions (including concentration of solution, temperature and cooling rate of solution), two or more kinds of crystals having different appearances are obtained similarly to the (NPTh) (TCNQ)$_2$ crystals. That is, crystals in the form of a needle, a rod or a cross therebetween are obtained. The resistivities of the typical crystals at a normal temperature are 5.0 to 7.0 Ωcm for needle crystals and 35 to 50 Ωcm for rod crystals, respectively.

It should be noted that the different types of the crystals show substantially the same resistivity-temperature characteristics when once heated to above 140° C. or more.

Resistivity-temperature Characteristics

The (NBPy)(TCNQ)$_2$ is powdered and press molded at a normal temperature to have a diameter of 3 mm and a length of about 10 mm. The molding is provided with 4 probes by means of silver paste and then subjected to a measurement of resistivity in relation to temperature.

Figure 2:
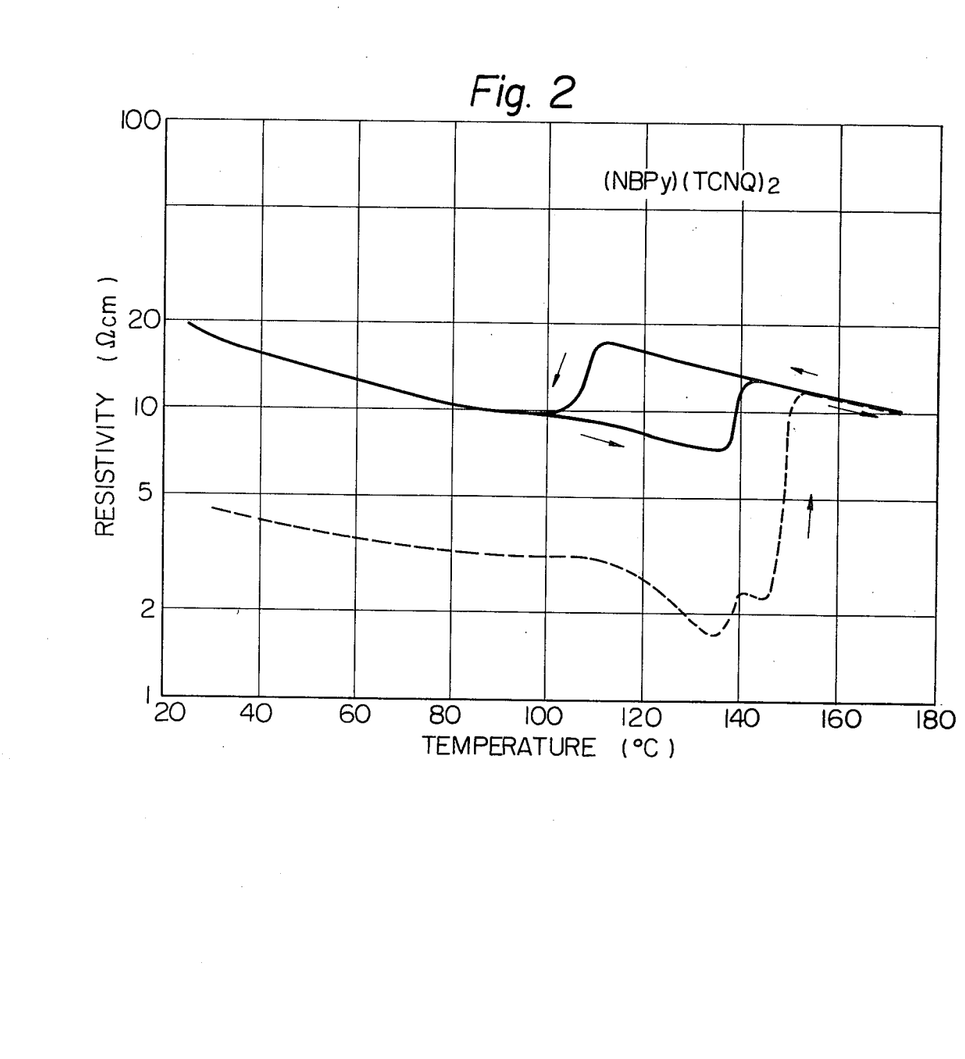
FIGS. 2, 3 and 4 are graphical representations similar to FIG. 1.

FIG. 2 shows the resistivity-temperature characteristic curves for (NBPy)(TCNQ)$_2$. The employed crystals are needle crystals obtained by the above-described method. The needle crystals are powdered in a mortar and press molded into the form of a bar. When the temperature is initially increased, the resistivity is irreversibly changed at 136° C. in a complicate manner (as indicated by dotted line in FIG. 2) and then settles into a stable state at temperatures of above 150° C. After completion of the initial irreversible changes, the reversible resistivity changes take place within a certain temperature range as shown by solid line.

These reversible resistivity changes are characterized by the following parameters tabulated below.

| Reversible Change Characteristics of (NBPy) (TCNQ)$_2$ | |
| --- | --- |
| parameter | numerical value |
| phase transition temperature under temperature-increasing conditions, $T_H$ (°C.) | 138 |
| phase transition temperature under temperature-decreasing conditions, $T_L$ (°C.) | 110 |
| variation rate of resistivity at $T_H$ (times) | 1.5–3.0 |
| resistivity at 125° C. $\rho_{125}$ (Ωcm) | 20 |

-continued

| Reversible Change Characteristics of (NBPy) (TCNQ)$_2$ | |
|---|---|
| parameter | numerical value |
| resistivity at 160° C. $\rho_{160}$ (Ωcm) | 11.2 |

The (NBPy)(TCNQ)$_2$ has its own resistivity-temperature characteristics, wherein the resitivity abruptly increases to about two times greater value when heated to 138° C., restoring its initial value at a lowered temperature of 110° C. That is, the hysteresis temperature of the (NBPy)(TCNQ)$_2$ complex is much greater than those of known inorganic PTC materials. Even if the (NBPy)(TCNQ)$_2$ compleses have different appearances or different resistivities immediately after the synthesis, they will show almost the same resistivity-temperature characteristics in the second and subsequent temperature cycles.

Similarly to the case of the (NPTh)(TCNQ)$_2$ complexes, the above-described anomal resistivity-temperature characteristics are considered to result from the first order phase transition accompanied by the crystalline rearrangements. This is confirmed by the observation of change in crystalline structure by the X-ray diffraction method and also by the differential scanning calorimeter (DSC). According to the DSC measurement, the latent heat of transition is absorbed at $T_H$ while the latent heat is emitted at $T_H$. The latent heat of transition ΔH of the (NBPy)(TCNQ)$_2$ ranges from 1.5–1.7 kcal/mole, which is greater than those of inorganic compounds. In the first order phase transition, it is rather rare that $T_H$ coincides with $T_L$. With inorganic compounds, the hysteresis within several centigrade usually occurs.

In this connection, however, the (NBPy)(TCNQ)$_2$ complexes have the hysteresis temperature as high as about 28° C., suitable to serve as heat-sensitive or timing elements.

The (NBTh)(TCNQ)$_2$ complex has the PTC characteristics similar to the (NBPy)(TCNQ)$_2$. The (NBTh)(TCNQ)$_2$ is characterized by an increase of resistivity to a 2 to 3 times greater value with heating to about 95° C. and by return to the original level with cooling to 70° C., in a reversible manner.

Synthesis

To a solution of 10 moles TCNQ in 200 liters of acetonitrile is added 7.5 moles of N-n-butylthiazolium iodide prepared by a known method, followed by reaction under gently refluxing conditions for 5 minutes. The reaction solution is allowed to stand in a thermostatic chamber of 5° C. overnight. The resulting black (NBTh)(TCNQ)$_2$ crystals are separated by a glass filter and washed with first acetonitrile and then ether to remove free iodine, and finally dried. By the reaction, the (NBTh)(TCNQ)$_2$ salt is obtained at a yield of 75 to 80%. The crystals thus obtained are purified by crystallizing the same in sufficiently purified acetonitrile 2 or 3 times. Two or more kinds of crystals having different appearances are obtained depending on the recrystallization conditions including concentration of solution, temperature and cooling rate of solution. That is, crystals in the form of a needle, a rod or a cross therebetween, are obtained. The resistivities of the typical crystals at a normal temperature are 110 Ωcm for rod crystals and 80 Ωcm for needle crystals, respectively. In this connection, however, even if the (NBTh)(TCNQ)$_2$ complexes has different appearances or different resistivities, they have almost the same resistivity-temperature characteristics in the repeated cycles of reversible resistivity changes.

Resistivity-temperature Characteristics

The (NBTh)(TCNQ)$_2$ complex is powdered and press molded at a normal temperature to give a molding having a diameter of 3 mm and a length of about 10 mm. The molding is provided with four probes by use of silver paste and its resistivity is measured in relation to temperature.

Figure 9:
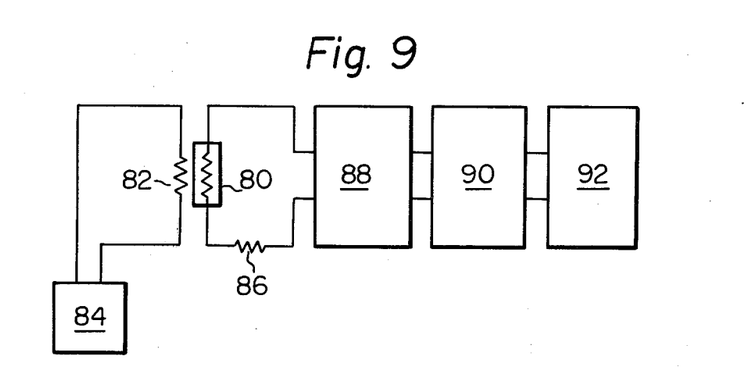
FIG. 9 is a block diagram showing a power control device for heat-sensitive or time limit elements according to the invention.

FIG. 9 shows the resistivity-temperature characteristic curves for (NBTh)(TCNQ)$_2$. When the temperature is initially increased, the resistivity is irreversibly changed at above 110° C. in a complicate manner as indicated by dotted line in FIG. 9, and then settles into a stable state at higher temperature.

After the initial irreversible changes, the reversible resistivity changes take place within a certain temperature range as indicated by solid line.

These reversible resistivity changes are characterized by the following parameters tabulated below.

| Reversible Change Characteristics of (NBTh) (TCNQ)$_{1+n}$ | |
|---|---|
| parameter | characteristic value |
| phase transition temperature under temperature-increasing conditions, $T_H$(°C.) | 90 |
| phase transition termperature under temperature-decreasing conditions, $T_L$(°C.) | 78 |
| variation rate of resistivity at $T_H$(times) | 2 |
| resistivity at 25° C., $\rho_{25}$(cm) | 4.6 |
| resistivity at 125° C., $\rho_{125}$(cm) | 3.6 |

Under temperature-increasing conditions, the resistivity of the heated (NBTh)(TCNQ)$_2$ abruptly increases at 90° C. to about 2 times greater value, returning to the original value at 78° C. The hysteresis temperature of the (NBTh)(TCNQ)$_2$ is very similar to that of the (NBpy)(TCNQ)$_2$. The latent heat of transition of this complex is 2.5 kcal/mole, which is much greater than those of inorganic compounds.

Three kinds of TCNQ-contained heat-sensitive materials which have been described hereinbefore may be added with conventionally employed additives to produce resistors having a desired level of resistivity. For example, graphic or metal powder such as silver powder is used to lower the resistivity of the complex materials according to the invention. The addition of the above-mentioned additives makes it possible to cause the temperature coefficient of resistance value close to zero. In order to increase resistivity of the complex materials, inorganic materials such as cement or a variety of polymers are useful.

The (NPTh)(TCNQ)$_2$, (NBpy)(TCNQ)$_2$ and (NBTh)(TCNQ)$_2$ may be further changed in $T_H$ and $T_L$ characteristics by substituting the cation with similar cations. For example, with (NBpy)(TCNQ)$_2$, part of NBpy cation may be replaced by N-n-propylpridium cation or N-n-hexypyridium cation, by which the $T_H$ and $T_L$ characteristics are arbitrarily changed to some extent depending on the degree of substitution. Likewise, with the (NBTh)((TCNQ)$_2$, part of NBTh cation may be replaced by N-n-propylthiazolium or N-n-hexylthiazolium cation. These replacements are readily feasible by adding desired amounts of such cations to the reaction system instead of corresponding amounts of NBPy or NBTh cations.

Further, the heat-sensitive complex materials of the invention may be improved in physical properties by adding thereto a binder resin. The binder resin is generally used in an amount of 2 to 20% by weight of a final composition. Larger amount will impair the heat-sensitive property of the complex materials while smaller amount will not assist in improving the physical properties. Examples of usable binder resins include ethylenevinylacetate copolymer, polyvinylbutyral, polyvinylpyrrolidone, polyurethane, polycarbonate, ethyl cellulose, chlorinated rubber, vinyl chloridevinyl acetate copolymer, polyvynilidene chloride, polyvinyl chloride, polyvinyl formal, polymethyl methacrylate, chlorinated polypropylene, nitrocellulose, rosin, cyclized rubber, etc.

According to a specific feature of the invention, the organic heat-sensitive materials of the invention are readily shaped into desired forms, i.e., into discs by press molding, into thick films by screen printing, into thin film by vacuum evaporation, etc., whichever is suitable as heat-sensitive or timing element.

The following discussion deals with applications, as heat-sensitive or timing element, of the organic heat-sensitive materials of the invention.

The organic heat-sensitive materials of the invention which have a hysteresis of temperatures above 10° C. and which have relatively low changes in electric resistance at the phase transition have particular utility in the field of timing elements. For instance, a control signal is given by heating or cooling the heat-sensitive or timing elements by a suitable means to start given operations, terminating the operations as soon as the reading variations of the electric resistance across the element reaches a preset value. Suitable selections of the organic heat-sensitive materials and control systems ensure the operating time within a range of several seconds to several tens hours.

The organic heat-sensitive materials of the invention have temperature hystreses of from 10° C. up to 65° C. and the time period of the phase transition in such materials may be changed in the range of several seconds to several tens hours. Although the reason why the phase transition takes place is not known at the present stage of our investigation, the sluggish transient phenomenon may be utilized to make electronic timing elements.

The electronic timing elements using the heat-sensitive materials of the invention operate on novel principles involving phase transition and are thus completely different from known counterparts or mechanical timing elements such as thermal timer, spring timer, motor timer, etc., electronic elements such as condenser timer and imcroprocessor. The timing elements according to the invention have the following advantages over the known ones: The known timing elements are incapable of controlling a long operating time, particularly operating times ranging from 2 to 10 hours and several hours, whereas the elements of the invention ensures the timing operation in a wider range of from several seconds to several tens hours, coupled with the advantage that they can be provided in a smaller size and at a low cost.

Figure 4:
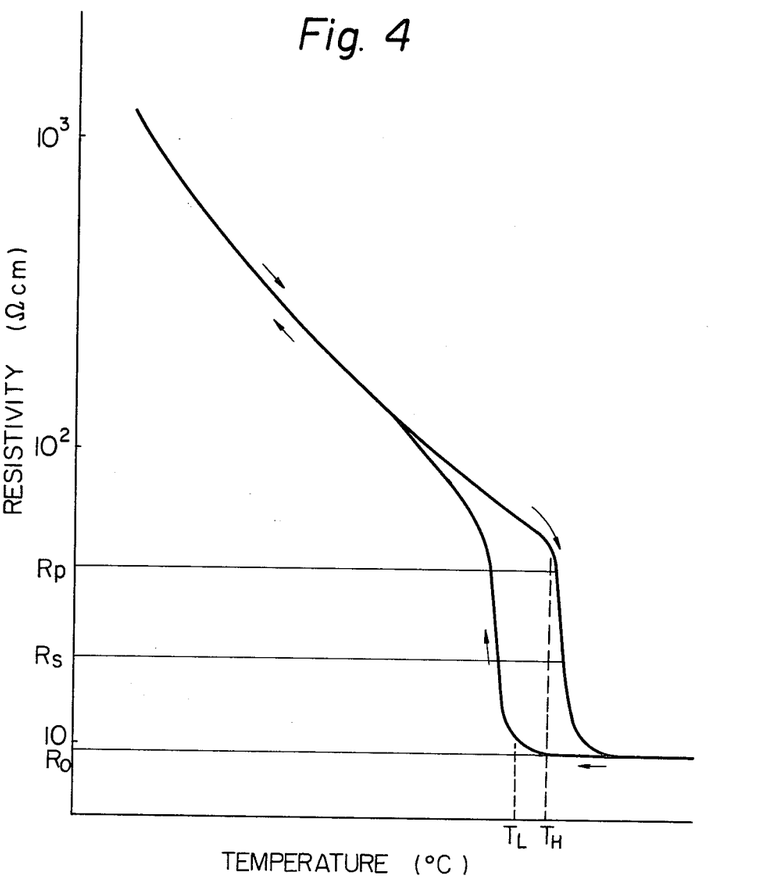

The timing action of the organic heat-sensitive materials of the invention will be illustrated with reference to FIG. 4, in which typical resistivity-temperature characteristics of a TCNQ complex are schematically shown by way of example. When the heat-sensitive complex material is heated above a normal temperature, the phase transition takes place at a temperature $T_H$, resulting in a material drop in resistivity. With cooling, no abrupt change in resistance takes place at or in neighbourhood of the temperature $T_H$ until the temperature is further lowered to below $T_L$. The heat-sensitive complex material has a resistance $R_o$ when heated up to a temperature higher than $T_H$ of FIG. 4, but when cooled down to temperature below $T_L$, its resistance gradually increases. When the timing value is pre-set at resistance $R_p$, the operation is limited to the time duration on which the resistance of the complex materials reaches from $R_o$ to $R_p$. When the resistance of the complex material increases gradually to a value $R_s$ intermediate between the $R_o$ and $R_p$, it is possible to maintain the resistance value $R_s$ for as long a period of time as desired by holding the temperature of the complex material between $T_L$ and $T_H$. In the above description, the timing operation is made by use of the resistance variations slowly occurring at temperatures below $T_H$. In this connection, however, the phase change at or in the vicinity of $T_H$ may be used for timing purpose.

The phase transition parameters and timing operation characteristics of the organic heat-sensitive materials of the invention are summarized in the following Table.

| heat-sensitive material | phase transition parameter | | | range of timing |
|---|---|---|---|---|
| | $T_H$(°C.) | $T_L$(°C.) | ΔT | |
| (NPTh) (TCNQ)$_2$ | 128 | 63 | 65 | 3 to 100 hours |
| (NBPy) (TCNQ)$_2$ | 134 | 110 | 24 | 10 seconds to 5 minutes |
| (NBTh) (TCNQ)$_2$ | 100 | 90 | 10 | 10 seconds to 10 minutes |

In the above Table, the ranges of timing are given merely as a measure and should be considered variable dependent on the type of control systems.

The timing element of the invention may be provided in the form of a small press molding or a film strip formed from organic heat-sensitive materials, with a pair of electrodes attached to the molding or film at a distance from each other, and a resin covering enclosing the press molding or film and the pair of electrodes. This element may be incorporated in an indirectly heating unit provided with one or more heaters.

Figure 5:
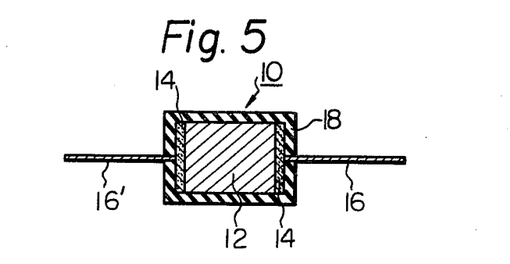
FIG. 5 is a schematical sectional view of a heat-sensitive resistor element using heat-sensitive semiconductive materials of the invention.

FIG. 5 shows generally at 10 a timing element using a press molding of the organic heat-sensitive materials of the invention. The element 10 includes a press-molded semiconductor 12, a pair of electrodes 14 provided at opposite sides of the press molding 12 in contact therewith, lead wire 16 connected with the pair of electrodes 14, respectively, and a resin covering 18 enclosing the entire assembly of the press molding 12 and the pair of electrodes 14. In this instance, the organic heat-sensitive material is powdered by reprecipitation or grinding. The powder is then pressed into a desired form such as cylinder, angled pillar or the like. Upon shaping, the heat-sensitive material may be mixed with any additives. For example, small amounts of polymers may be added to improve the molding in physical strengths. The electrode is usually made of silver paste or colloidal graphite (i.e, dag).

Figure 6:
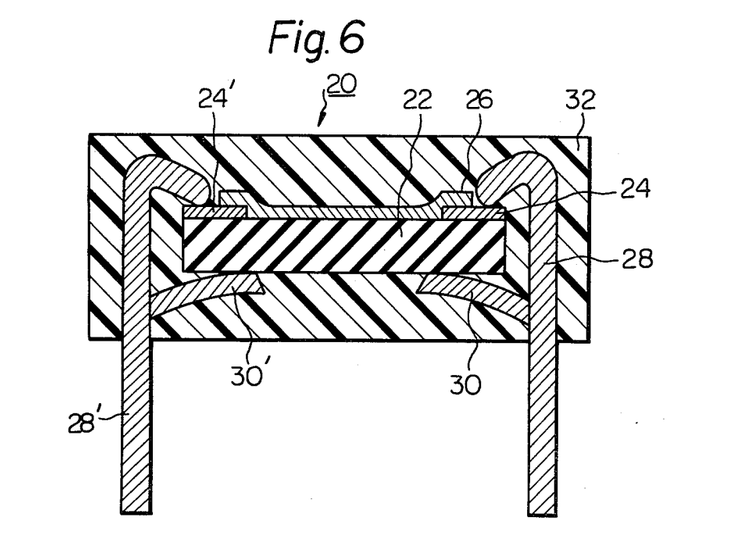
FIG. 6 is a schematical sectional view of another heat-sensitive resistor element using heat-sensitive semiconductive materials of the invention.

FIG. 6 shows another type of the timing element generally at 20. This timing element 20 comprises a ceramic substrate 22, a pair of electrodes 24 and 24' provided on one side of the substrate at a distance from each other, and a film of heat-sensitive material 26 formed on the substrate in contact with the pair of electrodes 24 and 24'. The pair of electrodes 24 and 24' have lead wires 28 and 28' with supports 30 and 30', respectively. The entire assembly of the timing element 20 is enclosed in an insulating resin covering 32. The heat-sensitive film 26 is formed by a printing method such as screen printing or gravure printing. In this instance, the organic heat-sensitive material of the invention is resuded to powder, preferably with as small a size as possible, in order to reduce the anisotory effect inherently possessed by crystals. In order to obtain finely powdered crystals, a vertical ball mill of super high speed revolutions is suitably used. The powdering is effectively feasible by use of an organic solvent such as cyclohexane, ether, or the like substance which is inert to the heat-sensitive materials. By powdering for about 8 hours, the powder size is reduced to 300 mesh or smaller. Then, the solvent is replaced by a solvent for screen gravure printing, to which is added a film-forming polymer binder. The mixture is treated for about 1 hour in a ball mill, whereupon the heat-sensitive powder is well dispersed in the polymer. The polymer useful as binder includes polyvinylpyrrolidone, polyvinylbutyral, an ethylenevinylacetate copolymer or the like. The solvent is, for example, n-butanol, benzyl alchol, monochlorobenzene or the like. The dispersion is applied onto the ceramic substrate 22.

Figure 7:
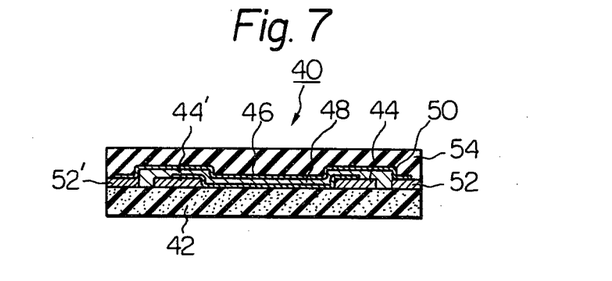
FIG. 7 is a schematical sectional view of a further heat-sensitive element using heat-sensitive semiconductor materials of the invention.

FIG. 7 shows an indirectly heated heat-sensitive or timing element 40. The element 40 includes an insulating heat-resistant substrate 42, a pair of electrodes 44 and 44' for heater formed on the substrate 42 at a distance, and a resistor or carbon film 46 formed on the substrate 42 in contact with the pair of electrodes 44 and 44' at the opposite ends thereof. The pair of electrodes 44 and 44' and the resistance film 46 are covered with an insulating layer 48 to electrically insulate an organic heat-sensitive semiconductive layer 50 from the resistance film 46. Designated at 52 and 52' are a pair of electrodes for the heat-sensitive layer 50. The upper surface of the substrate 42 is entirely covered with a resin covering for complete insulation.

Figure 8:
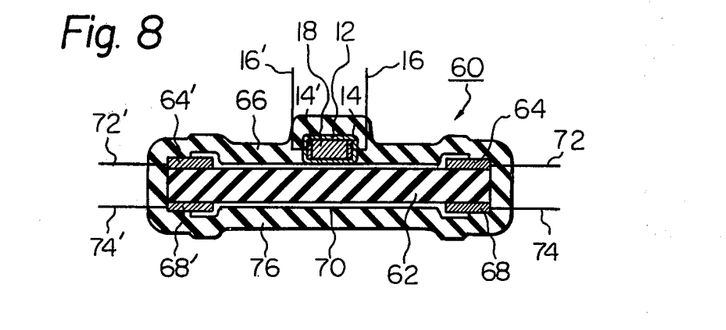
FIG. 8 is a schematical sectional view of a still further element according to the invention.

FIG. 8 illustrates still another embodiment of the invention, in which the element of FIG. 5 is used. This element is also an indirectly heated timing element provided with two heater units. The element 60 includes an insulating thin substrate 62 which is provided with, on one surface thereof, a pair of electrodes 64 and 64' for heater and a thin resistance film 66 such as of carbon. The ends of the film 66 are in contact with the pair of electrodes 64 and 64' for passage of electric current. Likewise, a pair of electrodes 68 and 68' and a thin resistance film 70 such as of carbon are provided on the other surface of the substrate 62. Indicated at 72 and 72' are lead wires for the electrodes 64 and 64' and at 74 and 74' are lead wires for the electrodes 68 and 68'. Indicated at 76 is a resin covering.

The operating modes of these timing elements may be changed, more or less, depending on the kind of the heat-sensitive material, but practical examples are:

1. Reset:
The element is directly or indirectly heated to temperatures above $T_H$ to reset the resistance thereof to an initial value $R_o$.

2. Operation:
The temperature of element is maintained at temperatures below $T_L$. The operating time is the time duration in which the resistance of the element reaches a pre-set value $R_p$.

3. Hold-on:
It is possible to electronically maintain the operation by keeping the element temperature between $T_L$ and $T_H$. Upon holding the element temperature between $T_l$ and $T_H$, the operations which have been experienced are memorized to maintain the hold-on.

4. Time Integration:
When the operations (2) and (3) are repeated, the operating time of the operation (2) is added.

A variety of electric circuits are usable for effecting the timing operation by use of these elements. As will be seen from the above, a resistance-dividing circuit is first required. A semiconductive element is used together with a relay or a power control circuit when high electric power is desired to be controlled.

Figure 13:
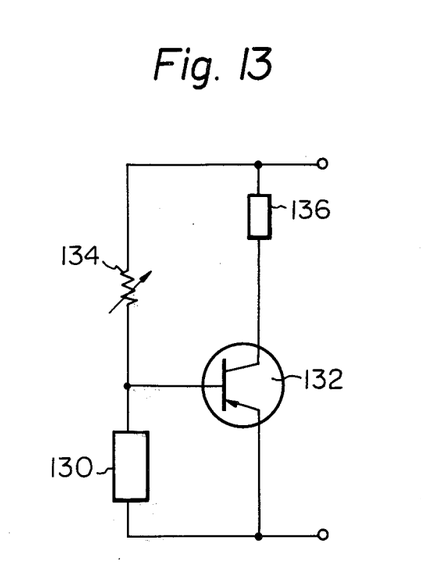

FIG. 9 is a power control circuit diagram, in which a disc or printed film-type element 80 according to the invention is combined with an indirect heater 82 of the same type as shown in FIG. 13. A heater-control circuit 84 is connected with the heater 82 to supply the reset and operating time control current. The element 80 is series connected to a variable resistor 86 for presetting the resistance. The integrated resistances of the element 80 and the variable resistor 86 are converted to a voltage by means of a resistance-voltage converter 88. In a voltage control circuit 90 an increase of increasing voltage is controlled and transmitted to a contact circuit 92. The above power control circuit is made only for experimental purpose. The operating time can be controlled by either the heater current, the variable resistor 86 or the upper limit of voltage of the voltage control circuit 90.

The present invention will be particularly illustrated by way of the following examples.

EXAMPLE 1

This example illustrates the fabrications of a thick film element using (NPTh) (TCNQ)$_2$ complex.

(NPTh) (TCNQ)$_2$ was prepared in the same manner as in Synthesis of (PNTh) (TCNQ)$_2$ using a N-n-propylithiazolium iodide to TCNQ ratio by mole of 1:1.

98 parts by weight of the (PNTh) (TCNQ)$_2$ and 2 parts of ethylene-vinyl acetate polymer were powdered in a mortar to give a heat-sensitive composition.

The heat-sensitive composition was shaped into a disc form having a diameter of 2-3 mm and a height of 0.5-1 mm. The disc was attached with a pair of carbon electrodes and applied with silver paste, from which lead wires were extended, respectively. The disc was covered with an epoxy resin for insulation and finally attached with a heater.

Figure 10:
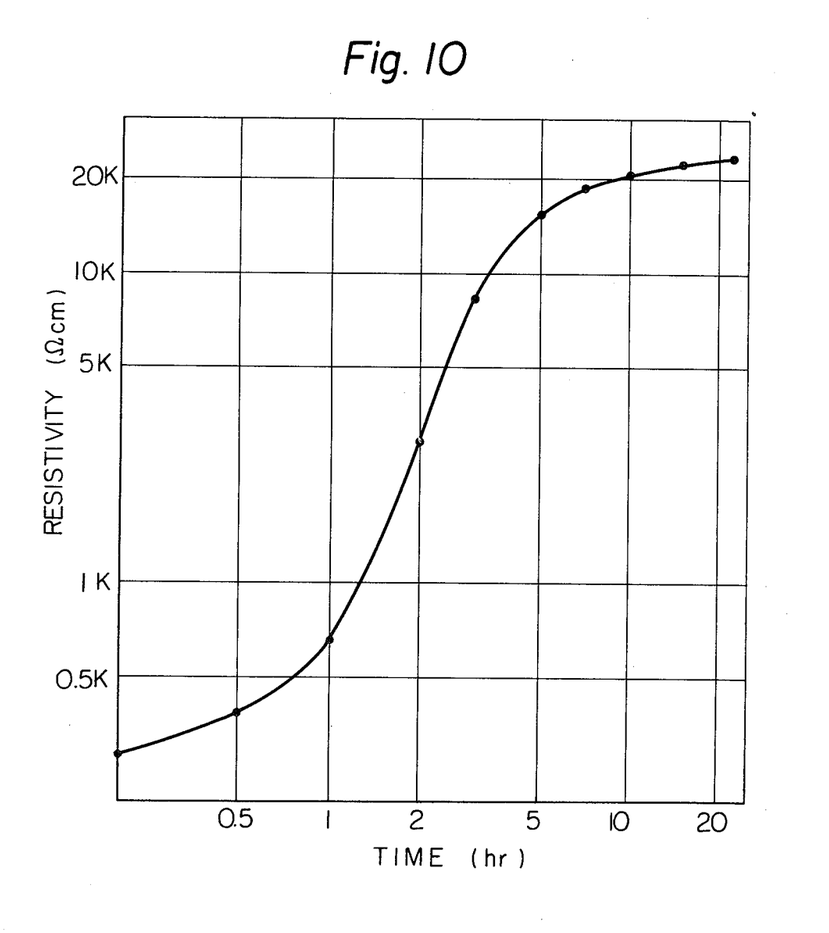
FIG. 10 is a graphical representation showing resistivity-time characteristics of a time limit element using a heat-sensitive material of the invention.

The resistivity-temperature characteristics of FIG. 10 were obtained by heating the element by the heater at temperatures above 140° C. and 10 minutes and allowed to stand at a normal temperature. The element had a timing range of 1 to 10 hours in the power control circuit of FIG. 9 by changing the present values of resistance. Further, when the element was maintained at a temperature of 40° to 50° C. by means of the heater during the operation, the changing rate of resistance was lowered and a timing control of 3 to several tens hours became possible.

EXAMPLE 2

The (PNTh) (TCNQ)$_2$ of Example 1 was used to make a heat-sensitive film by a printing method such as screen printing or gravure printing.

The heat-sensitive material was subjected to re-precipitation to obtain powder with an average size of 0.5 to 1μ. Larger size failed to give a printed film of uniform thickness. The powder was mixed with an ethylene-vinyl acetate copolymer (vinyl acetate content of 30%), to which was added cyclobenzene. The resulting dispersion was used for screen printing to make a heat-sensitive element of the type shown in FIG. 6. The polyemer to (NPTh) (TCNQ)$_2$ weight ratio was 1:4 and a 200 mesh stainless screen was used as printing mask.

Figure 11:
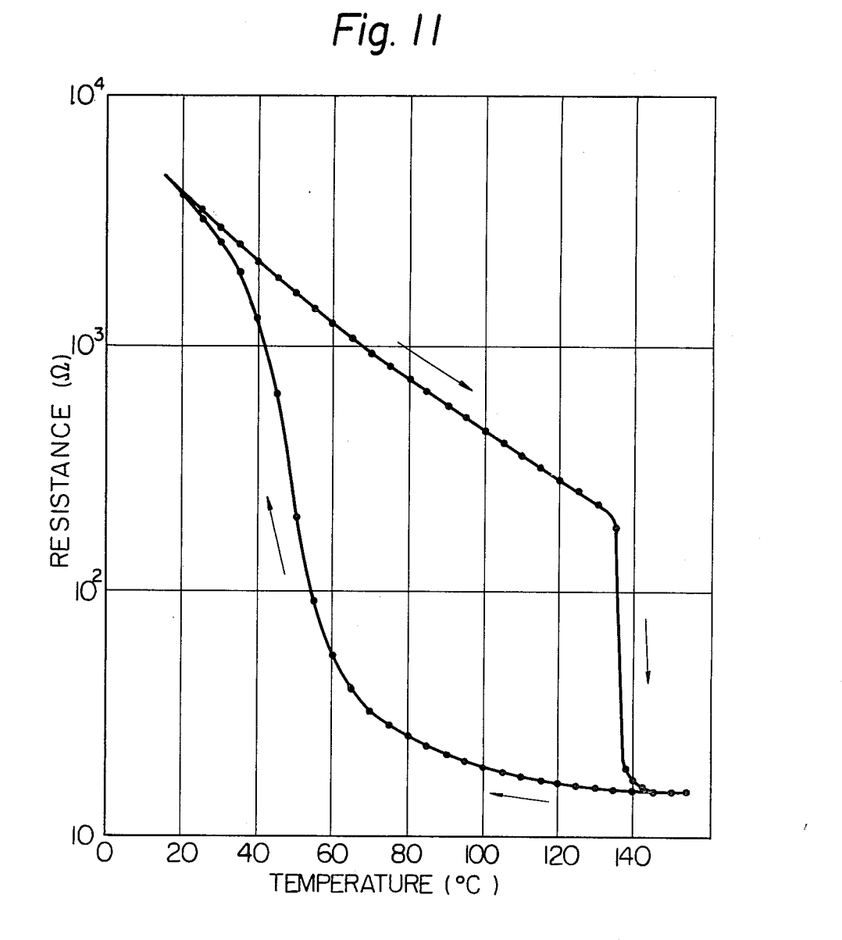
FIG. 11 is a graphical representation showing resistivity-temperature characteristics of a heat-sensitive material added with a polymer resin.

The resistance-temperature characteristics of the element are shown in FIG. 11. Upon comparing with the resistivity-temperature characteristics of (NPTh) (TCNQ)$_2$ alone shown in FIG. 1, the resistivity temperature characteristics of FIG. 11 are found to be poorer in the degree of resistance change and sharpness on lower temperature transition but substantially the same results were attained.

EXAMPLE 3

This example illustrates the application of the element of Example 1 as temperature switch.

Figure 12:
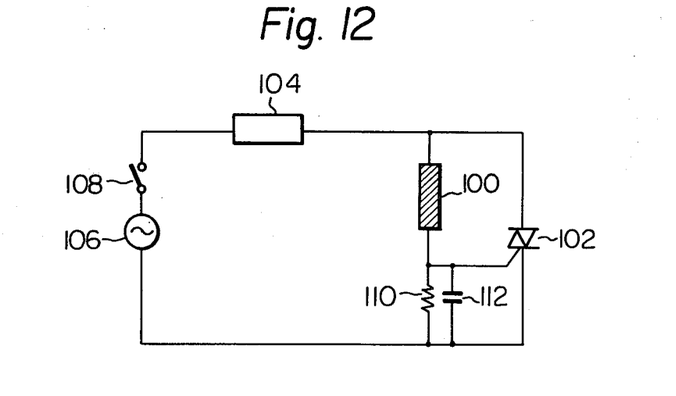
FIGS. 12 and 13 are circuit diagrams for temperature detection using heat-sensitive elements according to the invention.

The element was incorporated in a circuit as shown in FIG. 12, in which designated at 100 is a heat-sensitive element of the invention, at 102 a triac (i.e., bidirectional gate-controlled switching element), at 104 a load, at 106 a power source, at 108 a switch, at 110 a resistor and at 112 a capacitor when the element was heated to at temperatures above 130° C., the circuit was opened. The element was on when the temperature was decreased to below 50° C., not 130° C., due to the hysteresis of the heat-sensitive material as shown in FIG. 1. Thus the element could served as temperature switch of high fidelity.

EXAMPLE 4

This example illustrates film formation of the (NPTh) (TCNQ)$_2$ by vacuum evaporation.

An evaporation source (a tungsten bucket or a molbdenum boat) was maintained at a temperature of 220° C.±2° C., to which was changed powder of the heat-sensitive complex material. The powder used was obtained by, for example, a reprecipitation method to have an average size of 0.5 to 1μ. An evaporation substrate was placed at a distance of about 10 cm from the evaporation source and was maintained at a temperature above 80° C. so as to avoid the redissociation of one deposited substance. By the vacuum evaporation for 10 to 20 seconds, dark brown or black uniform film exhibiting an interference fringe was obtained. The film thickness was controlled by way of the evaporation time or the distance between the evaporation source and the substrate. When the material was vacuum evaporated to a thickness of 1μ or greater, the film surface become rough and gave rather poor electrical characteristics.

The resistivity-temperature characteristics of the evaporated film were just as shown in FIG. 1.

The heat-sensitive material vacuum-evaporated on a substrate with small heat capacity was capable of heat detection with high sensitivity.

EXAMPLE 5

This example illustrates fabrication of a thick film element using (NBPy) (TCNQ)$_2$ by a printing method.

(NBPy) (TCNQ)$_2$ was prepared in the same manner as in Synthesis of (NBPy) (TCNQ)$_2$ using a N-n-butyl-pyridium iodide to TCNQ ratio by mole of 1:1.

The thus prepared complex material was powdered in a vertical ball mill of super higher revolutions to have a 300 mesh size so as to reduce the anisotropy effect of the crystals. Upon powdering, an organic solvent such as chlorophexane, ether or the like which is inert to the (NBPy) (TCNQ)$_2$ was added to make effective powedering. After about 8 hours powdering, it was confirmed that the powder has a 300 mesh or smaller size. The solvent was then substituted with a solvent for screen printing, to which was added 10% by weight of polyvinylbutyral, followed by mixing in a ball mill for about 1 hour. The dispersion mixture was printed on a ceramic substrate in a desired pattern by a known technique. The substrate had been previously provided with a pair of electrodes at opposite ends of the substrate. The printed substrate was then treated at a temperature below 160° C. for several hours. Lead wires were connected to the electrodes on the heat-sensitive film. Finally, the substrate was covered with a resion covering for insulation.

The heat-sensitive element has at a normal temperature a resistance in the range of 10 kΩ to 10 MΩ, depending on the shape of the pattern. In either case, the resistivity-temperature characteristics had the same tendency as shown in FIG. 2. In order to determine the stability of the element in repeated use, the element was subjected to a temperature cycle test in which the temperature were varied between a normal temperature and 150° C. every cycle in about 10 minutes to determine variations of the characteristics parameters. As a result, it was found that the $T_H$ and $T_L$ temperatures were not changed at all after 500 cycles. However, the resistance was increased to about 1.2 times greater after the 500 cycles test.

EXAMPLE 6

This example illustrates application of the heat-sensitive element of Example 5 as a temperature switch.

For the above purpose, an alarm circuit of FIG. 13 was used in which designated at 130 is the heat-sensitive element of the invention which serves to control a base bias of a transistor 132. A variable resistance 134 was present at a predetermined value so that the transistor 132 became non-conductive at a temperature below $T_H$ and conductive at temperature above $T_H$. When the transistor 132 was rendered conductive, electric current was fed to a load 126 to operate a lump or buzzar.

The feature of this circuit is that the circuit is completed when the heat-sensitive element is heated to above the temperature $T_H$, and operated at temperatures below $T_L$, not below $T_H$.

EXAMPLE 7

This example illustrates fabrication of an indirected heated element of the type shown in FIG. 7, in which (NBPy) (TCNQ)$_2$ complex was used as a heat-sensitive material. The organic heat-sensitive film 50 was screen printed according to the method Example 8. The carbon film 48 to be an indirectly heating heater was designed to generate heat sufficient to operate the heat-sensitive element. That is, the heat-sensitive film 50 and the carbon film 48 were printed to have areas of 2×1 mm, respectively. The former film had a resistance of 10 KΩ and the latter film had a resistance of about 1 kΩ.

The indirectly heated heat-sensitive element may be widely applied to pulse circuits, oscillation circuits or delay circuits. In a most simple application, a heater is series connected to the heat-sensitive element, to which is applied a direct voltage of about 60 V. The direct current is oscillated at a frequency of about 1/10 herz as a result of the delay of response due to the PTC characteristics and great temperature hysteresis of the (NBPy) (TCNQ)₂ complex.

EXAMPLE 8

Figure 3:
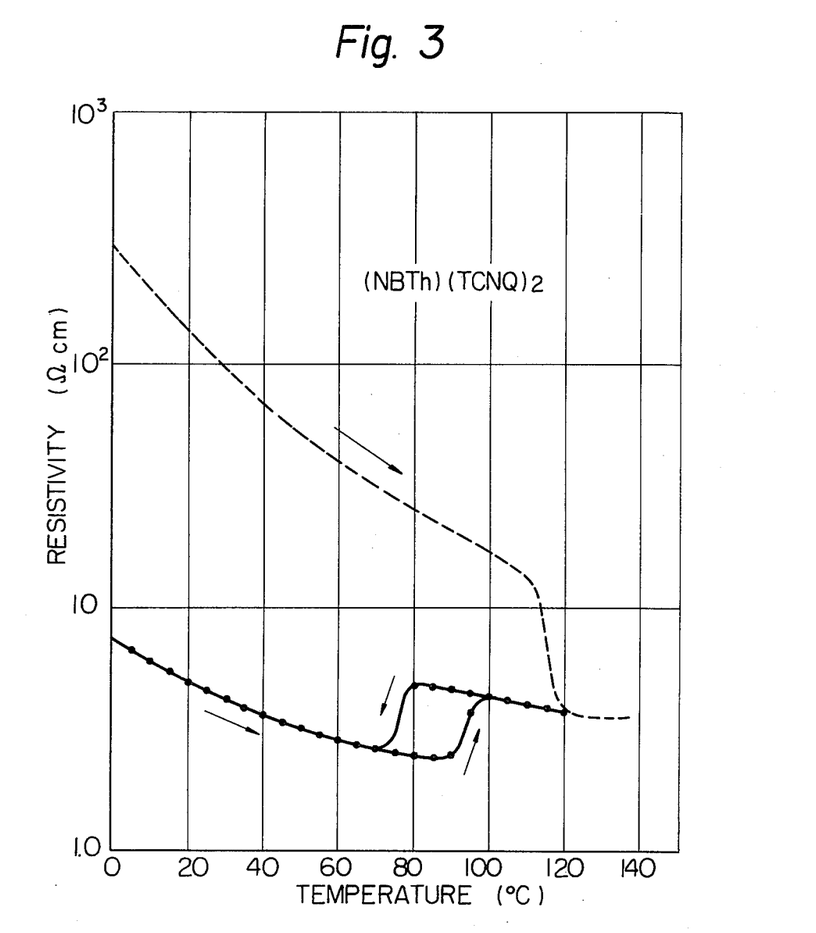

Example 5 was repeated using (NBTh) (TCNQ)₂ complex. The resulting heat-sensitive element using 10% by weight of polyvinylbutyral as binder had at a normal temperature a resistance of 100 to 100 MΩ, depending on the shape of the pattern. The resistivity-temperature characteristics of the element had the same tendency as shown in FIG. 3.

In order to determine the stability of the element in repeated use, the element was subjected to a temperature cycle test in which the applied temperature was changed between a normal temperature and 150° C. every cycle in about 10 minutes to determine variations of the characteristic parameter. As a result it was found that the $T_H$ and $T_L$ temperatures were not changed after 500 cycles. However, the resistance was increased to about 1.2 times greater after the 500 cycles test.

Similarly to the case of Example 6, this element was suitably applicable to an alarm circuit, with good results.

What is claimed is:

1. An organic heat-sensitive semiconductive material selected from the group consisting of:
   (a) (N-n-propylthiazolium)⁺(7,7,8,8-tetracyanoquinodimethane)⁻(7,7,8,8-tetracyanoquinodimethane) expressed by the following formula and
   (b) (N-n-butylthiazolium)⁺(7,7,8,8-tetracyanoquinodimethane)⁻(7,7,8,8-tetracyanoquinodimethane) expressed by the following formula 2. (N-n-propylthiazolium)⁺(7,7,8,8-tetrcyanoquinodimethane)⁻(7,7,8,8-tetracyanoquinodimethane) expressed by the following formula 3. (N-n-butylthiazolium)⁺(7,7,8,8-tetracyanoquinodimethane)⁻(7,7,8,8-tetracyanoquinodimethane) expressed by the following formula

* * * * *